United States Patent [19]

Haindl

[11] Patent Number: 4,889,529
[45] Date of Patent: Dec. 26, 1989

[54] NEEDLE

[75] Inventor: Hans Haindl, Melsungen, Fed. Rep. of Germany

[73] Assignee: B. Braun Melsungen AG, Melsungen, Fed. Rep. of Germany

[21] Appl. No.: 214,182

[22] Filed: Jul. 1, 1988

[30] Foreign Application Priority Data

Jul. 10, 1987 [DE] Fed. Rep. of Germany ....... 3722800

[51] Int. Cl.⁴ .............................................. A61M 5/32
[52] U.S. Cl. ................................................... 604/274
[58] Field of Search .............................. 604/272–274, 604/411

[56] References Cited

U.S. PATENT DOCUMENTS

| | | | |
|---|---|---|---|
| 2,697,438 | 12/1954 | Hickey | 604/274 |
| 2,711,733 | 6/1955 | Jacoby | 604/274 |
| 2,717,599 | 9/1955 | Huber | 604/274 |
| 3,788,119 | 1/1974 | Arrigo | 604/274 X |
| 4,808,170 | 2/1989 | Thornton et al. | 604/274 |

FOREIGN PATENT DOCUMENTS 1225009  6/1960  France ................ 604/272

Primary Examiner—Dalton L. Truluck
Attorney, Agent, or Firm—Spensley Horn Jubas & Lubitz

[57] ABSTRACT

One side wall of a rigid needle tube is provided at its front end with a curved bending directed towards the opposite, axial side wall and has a lumen opening formed therein. The lumen opening is provided with a rear inner cutting edge and a front punctuating portion which comprises a lancet-shaped tip having a facet grinding. The tip is arranged in a zone defined by two imaginary lines extending respectively from the inner surface and the outer surface of the axial side wall beyond the rear cutting edge of the lumen opening. When using the needle, no material is punched out of the material to be perforated.

10 Claims, 3 Drawing Sheets

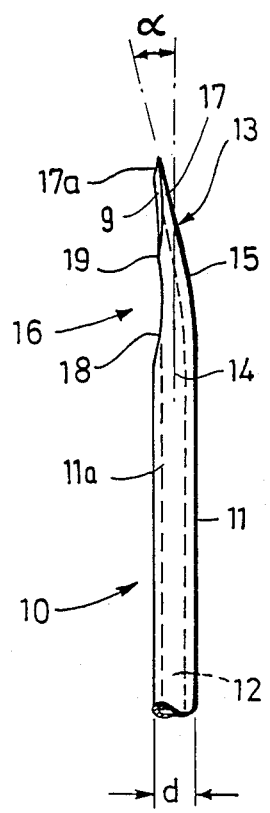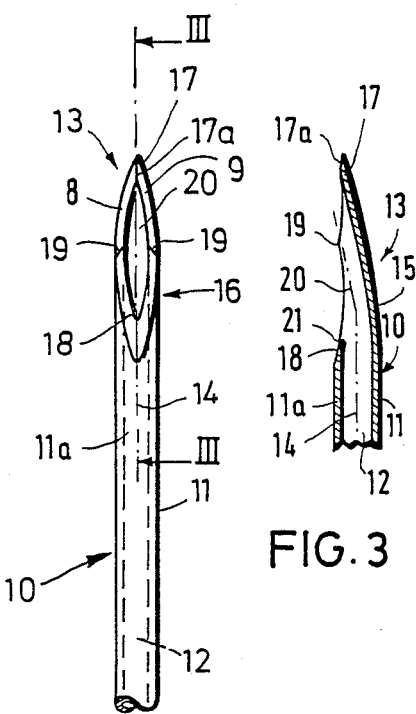
FIG.1 FIG.2 FIG.3

NEEDLE

BACKGROUND OF THE INVENTION

1. Field of the Invention

The invention is directed to a needle comprising a hollow rigid needle tube having one side wall at the front end of the needle tube which is curved toward the opposite, axial side wall. A lumen opening is formed in the axial side wall in a region near the curved side wall. The lumen opening extends substantially parallel to the longitudinal axis of the needle tube and is provided with a front punctuating portion and a rear inner cutting edge arranged on the inner surface of the axial side wall.

2. Description of Related Art

A known needle is disclosed in U.S. Pat. No. 2,746,454. Insertion of such a needle into a blood vessel without danger of hurting the opposite wall of the vessel is facilitated by the front punctuating portion of the needle being formed as a hook. The strongly curved back surface, opposite the comparatively short lumen opening, acts as a gliding surface. The foremost round edge of the punctuating portion is directed transversely to the longitudinal axis of the needle tube (towards the side) and is in alignment with the outer surface of the needle tube. The round edge is free of a plane bevel, whereas the rear edge of the lumen opening is beveled to thereby form an inner cutting edge.

For making good use of its curved sliding surface, a needle of this kind is inserted into a blood vessel along a curved path. The course of the curved path substantially corresponds to the radius of curvature of the sliding surface of the punctuating member. Due to this angular positioning of the needle during punctuation (which is unavoidable because of the hooked curvature), the sharp rear cutting edge of the lumen opening punches out material from the surface opening. The punctuating opening is thereby enlarged. This produces a disadvantageous traumatic effect when punctuating tissue.

This punching out effect (or punching effect) is also not desirable when the needle is used to refill a device for administering medication. Such a device for administering medication might comprise, for example, an implanted capsule having a cavity for receiving the medication and being connected to a catheter. The free end of the catheter would lead to an infusion site and would supply medication thereto. The outwardly directed wall (directed towards the skin of the patient) of the implanted capsule would consist of a perforable elastomeric diaphragm which is punctuated by the needle for refilling medication into the cavity of the capsule.

According to the prior art, repeated punctuating of a needle into the diaphragm of the capsule causes leakage of the diaphragm because the edge of the bevel eye punches out elastomeric material. This creates holes that do not close again by themselves. After a comparatively small number of punctures, the capsule starts leaking, thus forcing the user to exchange at least the capsule of the administering device. Besides, punched-out particles of the material that are carried along into the medication system cause contamination of the medication.

Up to now, so-called Huber needles have been used as refill needles. In one presently used embodiment of such Huber needles, the whole needle tube has its front end kinked obliquely sidewards. The front end of the needle tube section is provided with a lumen opening which extends substantially in parallel to the longitudinal axis of the needle tube and which is beveled circumferentially.

In such needles, the lumen opening is arranged far outside of the contour of the straight needle tube section. Even upon correct vertical positioning of the Huber needle, this fact causes material particles to be punched out. This is because the angled front portion of the needle tube, like a wedge, penetrates the surface from one side. The rear cutting edge of the bevel (which cutting edge is opposed to the wedge) is pressed laterally against the material to be penetrated and thus shears off material that has entered into the opening. When the needle tip is incorrectly pierced obliquely into the surface to be punctuated, even more wall material penetrates into the lumen opening. As a consequence, still larger material portions are sheared off by the exposed cutting edge of the rear bevel eye of the lumen opening.

In another embodiment of the Huber needle comprising a laterally directed lumen opening (U.S. Pat. No. 2,409,979), one side wall of the needle tube is diverted toward the opposite axial side wall obliquely and without curvature. The edging surrounding the lumen opening is ground flatly and tangentially to the outer surface of the needle tube and has its rear edge area provided with a cutting edge sloping from the outside to the inside, i.e. an outer cutting edge. The punctuating portion, the tip of which is in alignment with the outer circumference of the axial side wall, is provided with a facet grinding on the edging of the lumen opening.

Practice has shown that during punctuation of an artificial or natural surface, the oblique surface of the needle tube causes a one-sided wedge effect which impedes the formation of a non-widened, sharp cut. Upon advancing of the needle, material is pressed into the lumen opening. The material is cut off at the rear cutting edge and is damaged by squeezing.

The problem of considerable wall punchings by the rear cutting edge of a bevel eye also occurs when using another known needle (disclosed in DE-OS-No. 30 13 384) which is provided with a ground oblique lumen opening in its front region. A tip extends at an angle from the front end of the lumen opening. The outer end of the angled tip is arranged substantially on the central axis of the needle tube. The rear cutting edge of the bevel eye is arranged at the rear end of the lumen opening without the contour of the needle tube. When piercing a surface to be punctuated, a considerable punching effect is caused by an S-shaped curved path along which the tip is guided because of the mutual orientation of the parts of the front end of the needle tube. This punching effect is equally undesired when punctuating artificial and natural walls (diaphragm and body tissue).

It is an object of the present invention to improve the initially mentioned needle in such a manner that punching effects are eliminated during punctuation of a natural or artificial wall so that during use of the needle (e.g. as a spinal needle) damage to tissue is prevented, and during use of the needle as a refill needle the leak-proof condition of the implanted capsule of a device for administering medication is guaranteed even after several hundred punctuations.

SUMMARY OF THE INVENTION

In accordance with the present invention, these and other objectives are achieved by providing a needle in which the punctuating portion comprises a lancet-shaped tip having a facet grinding and being arranged in the zone between two imaginary parallel lines which continue the inner surface and the outer surface of the axial side wall forwardly beyond the rear cutting edge of the elongate lumen opening.

When a needle according to the present invention is used for punctuating artificial or natural walls, the punching effect is reduced. It is believed that this is because the position of the lancet-shaped and facet-grinding-sharpened tip of the punctuating portion in the radial zone of the axial wall, along with the curved bending of the rear side of the needle tube, provides for generation of a sharply defined slot without detrimental wedge-effects occurring in the wall to be pierced.

The slot is widened concentrically by the curved back opposite to the lumen opening until the outer diameter of the straight needle tube is attained. Each time the needle is drawn out, the slot closes tightly.

The combined features of the present invention facilitate the vertical punctuating direction of the needle, which is favorable for preventing the removal of material. The puncture remains small because the lateral offset of the tip of the punctuating portion with regard to the longitudinal central axis is compensated by the curving of the bend in such a manner that there is effected a puncture as performed by a central conical tip. Since the punctuating portion of the needle penetrates the cut slot in living tissue accurately, coaxially, and without lateral offset, tissue traumas are prevented and the healing process is accelerated. The knife-like cut through the layer of material, which is performed without removing material, allows up to several thousand leakage-free punctures of the elastic diaphragm of the implanted capsule of a device for administering medications. Thus, the capsule can remain implanted as long as required by the special therapy. Using said needle is easier on the patient because there is no repeated hypodermic implantation of the capsule and intrusion of punched-out particles into the body of the patient is prevented. Thus, the therapy becomes more reliable.

The beveled inner rear cutting edge of the lumen opening extends in alignment with the inner surface of the axial side wall of the needle tube. The tip of the punctuating portion is either positioned in alignment with the rear cutting edge or at any point between the imaginary extensions of the cutting edge and the outer circumference of the needle tube.

In an advantageous embodiment of the invention, the facet grinding is worked into the flat edge of the lumen opening. Cutting faces of a facet grinding are formed at both sides of the longitudinal central plane of the lumen opening of the needle tube and arranged in two planes. This effects a sharp and pointed tip of the punctuating portion. The facet grinding can terminate at the lumen opening. Alternatively, the facet grinding can terminate at a distance before the lumen opening. In this case, the facet grinding is restricted to a short part of the tip of the punctuating portion, and the flat edge surrounding the lumen opening is formed as an unfaceted closed bevel.

According to a further embodiment of the invention, the punctuating portion can have its back side provided with a facet grinding for forming the lancet-shaped tip of the punctuating portion. In this case, the whole edge of the lumen opening is enclosed by a surrounding smooth, flat edge bevel arranged in the plane of said lumen opening. This embodiment is inexpensive in production.

Even lower production costs are involved for manufacturing a needle wherein the punctuating portion has a sectional shape corresponding substantially to the section of a biconvex lens. In said embodiment, there exists no facet grinding, and sufficient separating sharpness is obtained by once beveling the edge which closely surrounds the lumen opening. With regard to the axial wall of the needle tube, the tip is arranged in the same manner as in the other embodiments of the invention, and a punching effect is prevented.

The beveled rear cutting edge of the lumen opening is preferably rounded inwardly. Said rounding contributes to preventing material from being punched out because, when the needle is penetrating the punctured surface, said rounding pushes off the material and by no means rubs it off.

The bending angle of the curved bending of the one side wall of the needle tube advantageously lies in an area from 13° + or − 3° and preferably amounts to 14°. The bending angle is defined as the angle between the longitudinal central axis of the needle tube and the tangent line plotted against the curved back side of the front end of the needle tube opposite to the lumen opening.

BRIEF DESCRIPTION OF THE DRAWINGS:

A detailed description of various embodiments of the invention will be made with reference to the accompanying drawings, wherein like numerals designate corresponding parts in the several figures.

FIG. 1 is a side view of a needle;

FIG. 2 is a plan view of the needle according to FIG. 1 as turned by 90°;

FIG. 3 is an enlarged lengthwise section of the punctuating portion of the needle according to FIG. 2 along the line III—III;

DESCRIPTION OF THE PREFERRED EMBODIMENT

Figure 4:
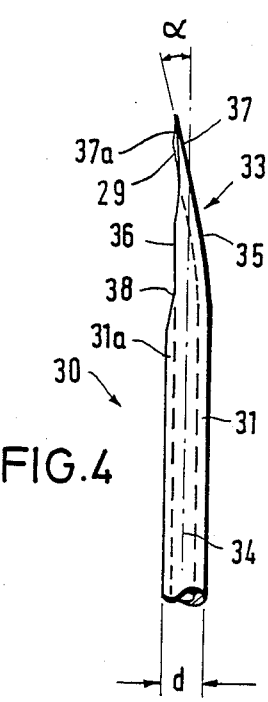
FIG. 4 is a side elevational view of a second embodiment of a needle.

The following detailed description is of the best presently contemplated mode of carrying out the invention. This description is not to be taken in a limiting sense, but is made merely for the purpose of illustrating the general principles of the invention. The scope of the invention is best defined by the appended claims.

The needle 10 according to FIGS. 1 and 2 consists of a hollow rigid cylindrical needle tube 11 made of metal. The rear end of the needle tube is connectable, (e.g. to an injection syringe or a hose or the like) for connection of a fluid transfer system. Along the largest part of the length of the needle tube 11, the needle tube extends straight. In the embodiment shown in FIGS. 1 and 2, the outer diameter d of the needle tube is 0.7 mm. The through-channel 12 may have a diameter of 0.4 mm.

For forming a punctuating portion 13, the front end of the needle tube 11 is curved at one side wall and bent obliquely in a lateral direction. The opposite side wall 11a remains in axial course. This provides an oval lumen opening 20, i.e. an opening which connects the longitudinal channel 12 (the lumen) of the needle tube 11 to the outside.

The lumen opening 20 extends substantially parallel to the longitudinal axis 14 of the needle tube and has a circumferentially beveled edge 16. The bending runs along the length of the lumen opening 20. The front half of the edge 16 is formed as a facet grinding with two grinding surfaces 8 and 9. The two grinding surfaces 8 and 9 are symmetrically arranged in two planes such that an axially oriented sharp tip 17 is generated at the leading bevel eye.

The bevel of the rear half of the edge 16 forms a rear bevel eye with a curved sharp cutting edge 18 which lies on the inner surface of the axial side wall 11a. The sharp cutting edge 18 is rounded by glass bead jets at 21 (FIG. 3).

The two bevel eyes are separated from each other by two oblique ridges 19, and the beveled part of the rear bevel eye between the ridges 19 and the cutting edge 18 extends concavely (FIG. 1). In this manner, the cutting edge 18 of the rear bevel eye remains free from bending, as in the facet grinding of a typical non-angled straight injection needle. In other words, the cutting edge 18 does not protrude outwardly beyond the contour of the needle tube 11. Instead, the cutting edge 18 is arranged within the contour by the amount of the wall thickness of the needle tube 11.

The tip 17 comprises an oblique, sharp punctuating edge 17a which extends axially and from which the bevel surfaces 8 and 9 of the facet grinding extend symmetrically towards both sides and to the ridges 19. The tip 17 is arranged substantially in alignment between two imaginary parallel lines that originate from the inner surface and the outer surface of the axial side wall 11a of the needle tube 11 in the forward direction.

The punctuating and cutting portions of the needle tube 11 are arranged within the contour of the needle tube 11 in the zone of the wall thickness of the axial side wall 11a. This prevents particles from being punched out of the natural or artificial layer of material to be penetrated, and outstanding separating characteristics are obtained. Here, the term "natural layer of material" is used for tissue that is penetrated when the needle 10 is used as a spinal needle. For example, a natural layer of material would be an elastomeric membrane in an implanted capsule of a system for administering medication.

The length of the bending of the back side 15 of the punctuating portion 13 between the outer point of the tip 17 and the cutting edge 18 of the lumen opening 20 is 3.6 d, + or − 0.42 d, in the illustrated example. Within the required tolerance the length can be greater, provided that it remains within the region of the bevel.

The bending angle between the longitudinal central axis 14 of the needle tube 11 and the tangent line plotted against the curved bent back side 15 of the punctuating portion 13 of the needle tube 11 is preferably 13° + or − 1°.

The lumen opening 20 of the needle tube 11, surrounded by the beveled edge 16 and directed to one side, is formed as an elongated double lancet. Both longitudinal halves of the lancet are symmetrical to the plane extending through the longitudinal axis 14 of the needle tub 11. The front transverse half of the lancet comprises the facet grinding 8 and 9.

Figure 5:
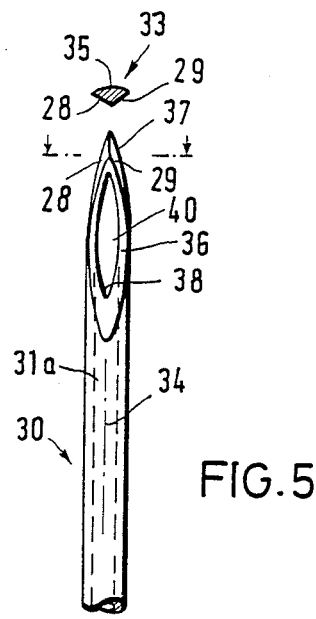
FIG. 5 is a plan view of the needle according to FIG. 4 as turned by 90°.

In the embodiment according to FIGS. 4 and 5, a rigid needle tube 31 of a needle 30, which is formed as a circular cylinder, is provided with an altered punctuating portion 33. The oval lumen opening 40, which is substantially parallel to the longitudinal axis 34 of the needle tube, is surrounded by an edge 36 which is surrounded by a plane-surfaced grinding. The rear edge of the lumen opening 40 forms a sharp cutting edge 38 which lies on the inner surface of the axial side wall 31a and which can be rounded inwardly, as FIG. 3 shows.

At the tip 37, the plane-surfaced grinding of the edge 36 is joined by a facet grinding. The facet grinding is composed of two ground surfaces 28 and 29 which are symmetrically arranged in two planes and which run into each other at a sharp axial punctuating edge 37a of the tip 37 of the punctuating portion 33.

Also in this example, the tip 37 along with the punctuating edge 37a is arranged between imaginary parallel lines which continue the inner surface and the outer surface of the axial side wall 31a beyond the rear cutting edge 38 of the lumen opening 40 in the forward direction. By this configuration, it is provided that practically no particles are punched out of the layer of material to be penetrated.

FIG. 5 is a section of the punctuating portion 3 within the region of the facet grinding. The curved back side 35, along which the opposite lumen opening 40 is arranged, has a preferred length of approximately 3.6d, + or − 0.42d. Also in this example, the bending angle alpha can amount to 13° + or − 1°.

Figure 6:
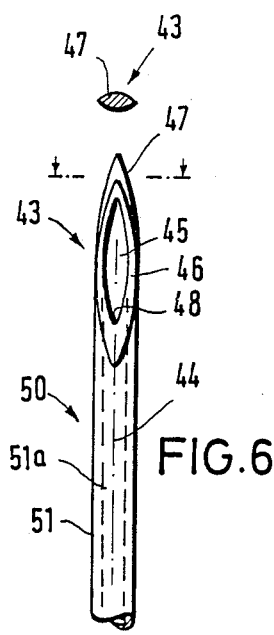
FIG. 6 is a plan view of a third embodiment of a needle.

FIG. 6 shows a section of a punctuating portion 43 of a further embodiment. In this embodiment a lumen opening 45 is laterally directed and substantially parallel to the longitudinal axis 44 of a needle tube 51 of a needle 50. The lumen opening 45 is enclosed by a surrounding plane-surfaced ground edge 46, leaving the tip area 47 free. The rear edge of said lumen opening 45 forms a sharpened inner cutting edge 48. As shown in Fig. 3, the cutting edge 48 can be rounded inwardly. Outside of the ground edge 46, the tip 47 of the punctuating portion 43 has a sectional shape resembling the section of a biconvex lens having a sharp edge. With regards to the linear axial side wall 51A of the needle tube 51, the tip 47 of the punctuating portion 43 is arranged in a manner corresponding to the tips 17 and 37 of the preceding examples.

Figure 7:
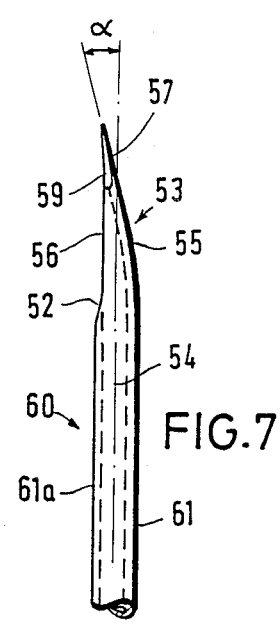
FIG. 7 is a side elevational view of a fourth embodiment of a needle.
Figure 8:
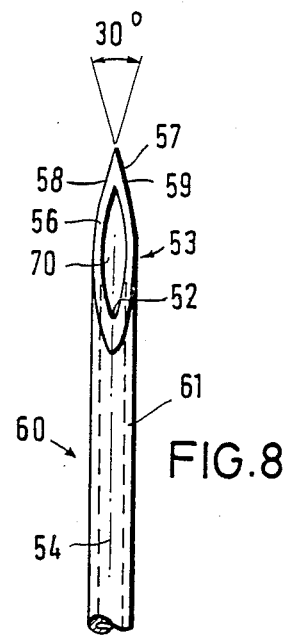
FIG. 8 a plan view of the needle of FIG. 7 as turned by 90°.

According to FIGS. 7 and 8, the front end of a needle tube 61 of a needle 60, forming a rounded bent back side 55, is provided with a punctuating portion 53. The punctuating portion 53 comprises a laterally directed lumen opening 70 extending substantially parallel to the longitudinal axis 54 of the needle tube 61. The edge 56 of the lumen opening 70 is ground to form a plane surface and completely encloses the lumen opening 70. The rear edge of the lumen opening 70 forms an inner cutting edge 52. A tip 57 of the punctuating portion 53 is laterally offset with regard to the longitudinal axis 54 of the needle tube 61 and is sharpened in that its back side 55, i.e. opposite to the ground edge 56, is provided with a facet grinding, which is called a rear grinding having two ground surfaces 58, 59. Preferably, the ground surfaces 58 and 59 of the facet grinding, extending in two planes, comprise an angle of 30°. In this example, the edge 56 of the lumen opening 70 is straight and plane-surfaced from the rear cutting edge 52 to the tip 57. The arrangement of the tip 57 with regard to the axial side wall 61a of the needle tube 61 corresponds to that of the preceding examples.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A needle comprising:
   a hollow, rigid needle tube having a longitudinal axis and including a front end, a first side wall and an opposite, axial side wall,
   the axial side wall having an inner surface and an outer surface,
   the first side wall being bent near the front end of the needle tube in a curve directed towards the opposite, axial side wall,
   a lumen opening defined in the axial side wall at a region adjacent the curve of the first side wall and extending substantially parallel to the longitudinal axis of the needle tube,
   the lumen opening having a front punctuating portion and a rear cutting edge arranged adjacent the inner surface of the axial side wall,
   the front punctuating portion comprising a lancet-shaped tip having a facet grinding and being arranged in a zone between two imaginary lines extending respectively from the inner surface and the outer surface of the axial side wall beyond the rear cutting edge of the lumen opening.

2. A needle according to claim 1, wherein the lumen opening includes a flat edge and the facet grinding is integrated with the flat edge of the lumen opening.

3. A needle according to claim 2, wherein the facet grinding terminates at the lumen opening.

4. A needle according to claim 2, wherein the facet grinding terminates at a distance spaced from the lumen opening.

5. A needle according to claim 1, wherein the punctuating portion includes a back side and the facet grinding is in the form of a rear bevel on the back side of the punctuating portion.

6. A needle according to claim 1, wherein the rear cutting edge of the lumen opening is rounded inwardly.

7. A needle according to claim 1, wherein the needle tube has an outer diameter equal to d and wherein the curve of the first side wall extends over a lengthwise area substantially between 2d and 5d.

8. A needle according to claim 1, wherein the curve of the first side wall bends at an angle substantially between 10° and 16°.

9. A needle according to claim 8 wherein the curve of the first side wall bends at an angle substantially equal to 14°.

10. A needle comprising:
    a hollow, ridge needle tube having a longitudinal axis and including a front end, a first side wall and an opposite, axial side wall,
    the axial side wall having an inner surface and an outer surface,
    the first side wall being bent near the front end of the needle tube in a curve directed towards the opposite, axial side wall,
    a lumen opening defined in the axial side wall at a region adjacent the curve of the first side wall and extending substantially parallel to the longitudinal axis of the needle tube,
    the lumen opening having a front punctuating portion and a rear cutting edge arranged adjacent the inner surface of the axial side wall,
    the punctuating portion having a cross section substantially in the shape of a biconvex lens and having a tip arranged in a zone between two imaginary lines extending respectively from the inner surface and the outer surface of the axial side wall beyond the rear cutting edge of the lumen opening.

* * * * *